United States Patent
Ohto et al.

[11] Patent Number: 5,505,211
[45] Date of Patent: Apr. 9, 1996

[54] BIOPSY NEEDLES

[75] Inventors: Masao Ohto; Chikara Nakao, both of Chiba; Takefumi Daido; Tetsuo Sekine, both of Tokyo; Masaru Maruyama, Nagano, all of Japan

[73] Assignee: Hakko Electric Machine Works Co., Ltd., Nagano, Japan

[21] Appl. No.: 250,800

[22] Filed: May 27, 1994

[30] Foreign Application Priority Data

May 16, 1994 [JP] Japan ................................ 6-125742

[51] Int. Cl.⁶ .................................................. A61B 10/00
[52] U.S. Cl. ........................... 128/754; 128/753; 128/749
[58] Field of Search ............................. 128/660.09, 749, 128/750, 751, 752, 753, 754, 755

[56] References Cited

U.S. PATENT DOCUMENTS

| | | | |
|---|---|---|---|
| 3,929,123 | 12/1975 | Jamshidi . | |
| 3,995,619 | 12/1976 | Glatzer ................... | 128/749 X |
| 4,517,965 | 5/1985 | Ellison et al. ........................ | 128/754 |
| 4,671,292 | 6/1987 | Matzuk ................ | 128/660.09 |
| 4,907,599 | 3/1990 | Taylor ....................... | 128/754 |
| 4,958,625 | 4/1990 | Bates et al. ........................ | 128/749 X |
| 5,127,419 | 7/1992 | Kaldany .................... | 128/754 |
| 5,188,118 | 2/1993 | Terwilliger ..................... | 128/754 X |
| 5,224,470 | 7/1993 | Schnepp-Pesch et al. ............ | 128/753 |
| 5,226,426 | 7/1993 | Yoon ...................... | 128/753 |
| 5,282,477 | 2/1994 | Bauer ...................... | 128/754 |

FOREIGN PATENT DOCUMENTS

| | | |
|---|---|---|
| 0390528 | 10/1990 | European Pat. Off. . |
| 1117258 | 11/1961 | Germany . |
| 2435123 | 7/1974 | Germany . |

*Primary Examiner*—Sam Rimell
*Attorney, Agent, or Firm*—Helfgott & Karas

[57] ABSTRACT

The set of biopsy needles of the invention is provided with a shaft member for an inner needle 6 which has an inner needle base 22 at the front end to fix an inner needle 24, a shaft member for an outer needle 13 which has an outer needle base 21 at the front end to fix an outer needle 23, a gripping member 1 for operation which fixes the shaft member for the inner needle 6 and axially movably support the shaft for the outer needle 13, a actuating member 9 which gives protrusion force to the shaft member for the outer needle 13, a holding member 15 which holds the shaft member for the outer needle 13 at the position before protrusion against the protrusion force of the actuating member 9 and releases from holding the shaft member for the outer needle 13 before protrusion by outside operation, and a rotation generating member 10 which gives rotation force to the shaft member for the outer needle 13 when the shaft member for the outer needle 13 moves axially.

3 Claims, 6 Drawing Sheets

BIOPSY NEEDLES

FIELD OF THE INVENTION

The invention relates to a set of biopsy needles for collecting tissue in a human body by an outer needle, and more particularly a set of biopsy needles by which the performance to cut off tissue can be enhanced and collection of tissue can be done easily and surely to provide enhanced reliability.

BACKGROUND OF THE INVENTION

At present, a set of biopsy needles is generally used to collect tissue in the affected part in a human body.

The set of biopsy needles comprises double needles composed of an outer needle in the form of a hollow tube and an inner needle to be inserted into the outer needle. It is punctured into an predetermined part in a human body and thereafter the outer needle is pushed forward to protrude from the tip of the inner needle whereby the tip of the outer needle can cut tissue in the affected part and the tissue can be collected inside the tip of the outer needle. Thereafter, the double needles is pulled back from the human body so that the tissue in the predetermined part can be collected.

In the conventional set of biopsy needles, however, the double needles can not surely cut off and collect the tissue in the affected part because the outer needle can cut off the tissue in the affected part by being protruded straightly, that is, only by being pushed and cutting after the double needles is punctured into the predetermined part in the human body.

SUMMARY OF THE INVENTION

Accordingly, it is an object of the invention to provide a set of biopsy needles by which the performance to cut off tissue can be enhanced and collection of tissue can be done easily and surely to provide enhanced reliability.

According to the invention, a set of biopsy needles comprises a shaft member for an inner needle which has a needle base to fix the inner needle at the tip, a shaft member for an outer needle which is located at the circumference of the shaft member for the inner needle and has a needle base to fix the outer needle at the tip, a gripping member for operation which is located at the circumference of the shaft member for the outer needle and fixes the shaft member for the inner needle and supports axially movably the shaft member for the outer needle, a actuating member which gives protrusion force to the shaft member for the outer needle so that the outer needle can protrude from the tip of the inner needle, a holding means which holds the shaft member for the outer needle at the position before protrusion against the protrusion force of the actuating member and releases the shaft member for the outer needle from holding by outside operation, a rotation generating means which gives rotation force to the shaft member for the outer needle to protrude the outer needle from the tip of the inner needle while being rotated when the shaft member for the outer needle moves axially by the protrusion force of the actuating member.

The above-mentioned holding means comprises a first circular magnetic plate which is fixed at the circumference of the shaft member for the outer needle and can be rotated by the outside operation, a second circular magnetic plate which is fixed at a predetermined position inside a main body tube, each of the first and second circular magnetic plate is circumferentially provided with a plurality of N and S poles which are located alternately.

The above-mentioned rotation generating means comprises a guide pin which is attached inside the gripping member for operation, a spiral groove which is formed on the circumference of the shaft member for the outer needle and is engaged with the guide pin. Alternatively, the spiral groove can be formed inside the gripping member and the guide pin is attached on the circumference of the shaft member for the outer needle.

According to the set of biopsy needles of the invention on the basis of the above construction, if the outside operation is done in order to release the shaft member for the outer needle from holding at the position before protrusion, then the shaft member for the outer needle is pushed forward by the protrusion force of the actuating member and rotation force is given to the shaft member for the outer needle by the rotation generating means, so that the outer needle is protruded from the tip of the inner needle while being rotated. Because of this, the tissue in the affected part in a human body is cut off by pushing and pulling force, whereby the performance to cut off can be enhanced.

BRIEF DESCRIPTION OF THE DRAWINGS

The invention will be described in detail in accordance with the following drawings wherein.

DESCRIPTION OF THE PREFERRED EMBODIMENT

Figure 1:
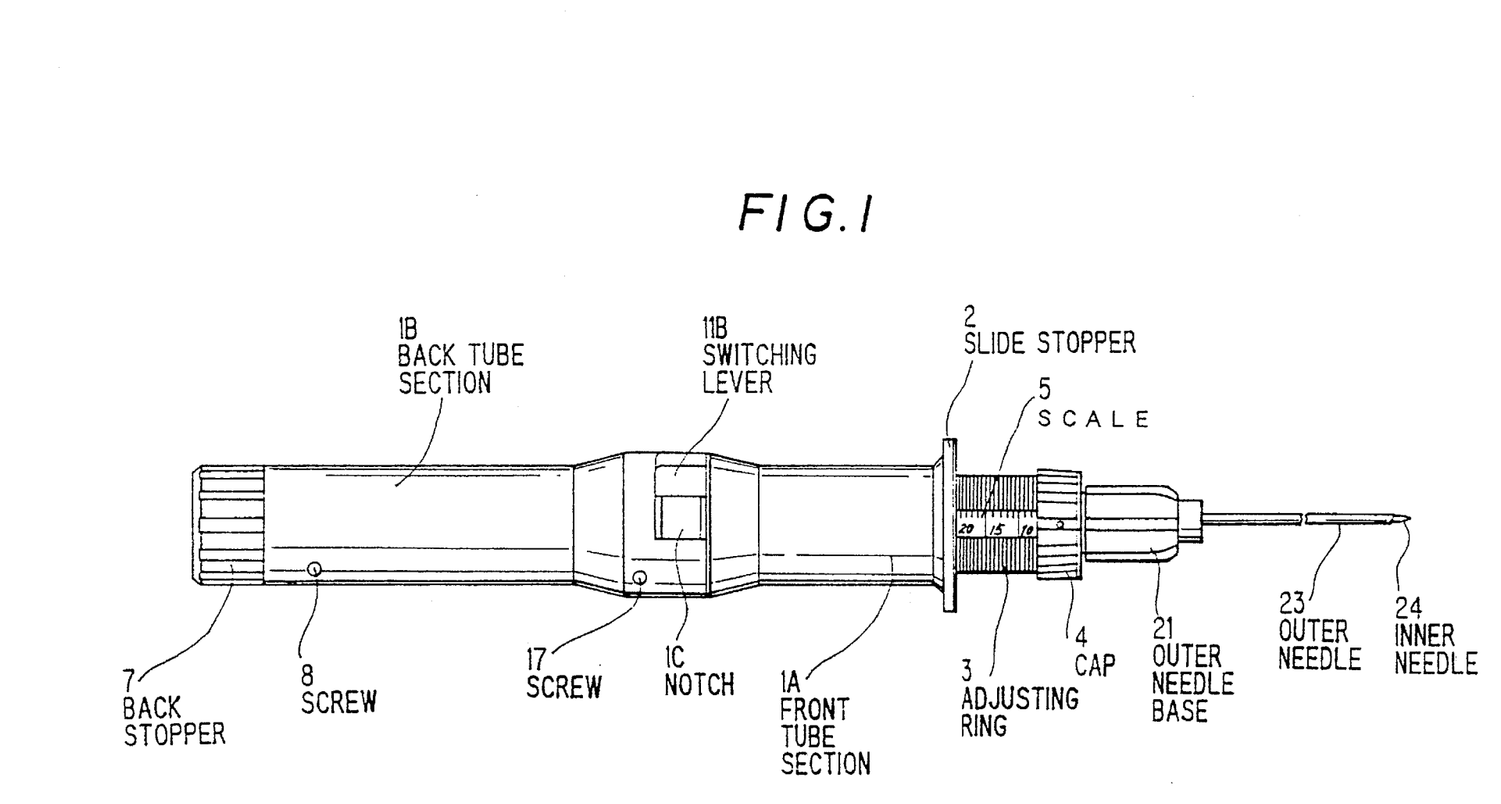
FIG. 1 is a explanatory view illustrating a set of biopsy needles in the first embodiment according to the invention.
Figure 2:
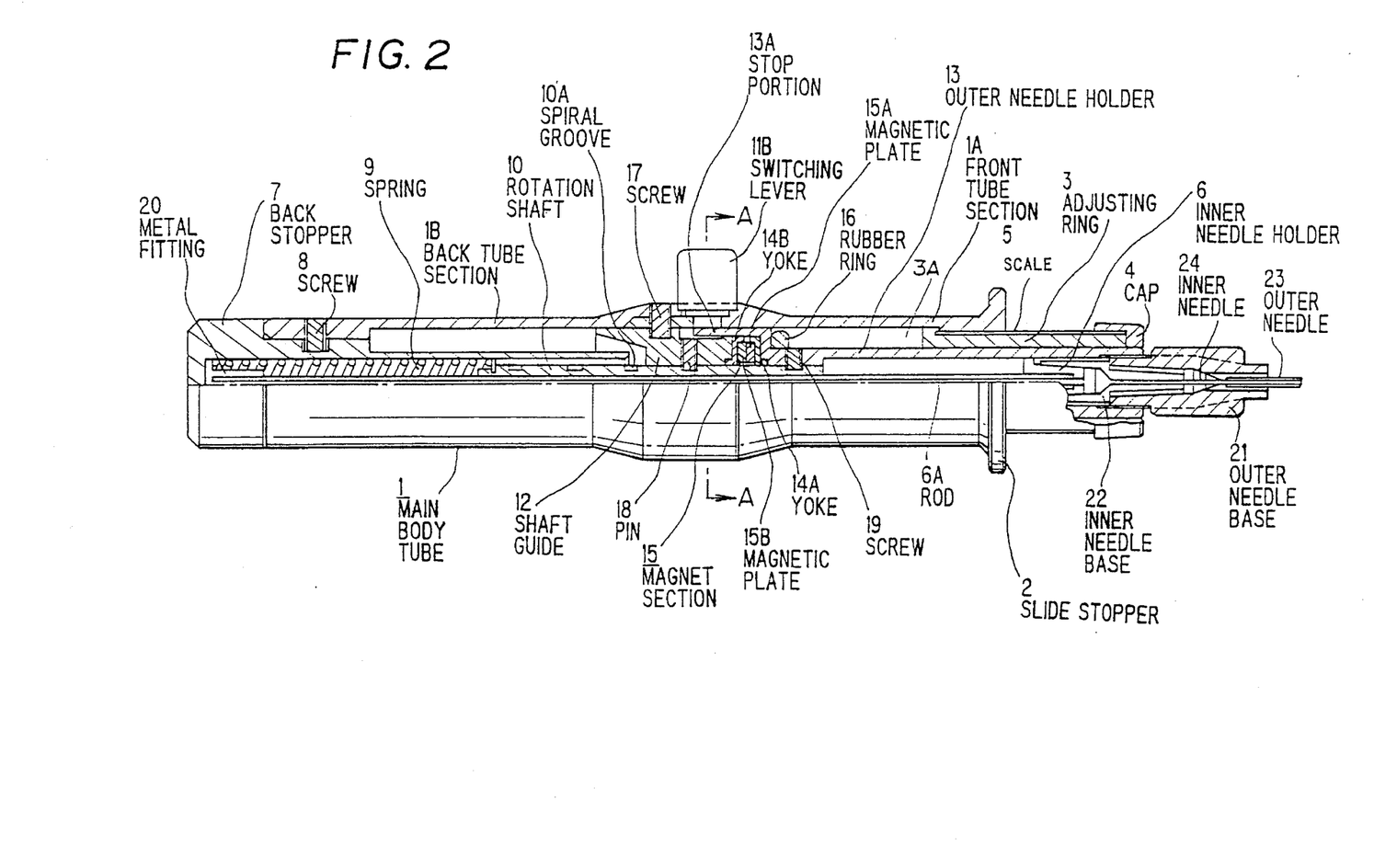
FIG. 2 is a partly cross-sectional view illustrating a set of biopsy needles in the first embodiment according to the invention.
Figure 3:
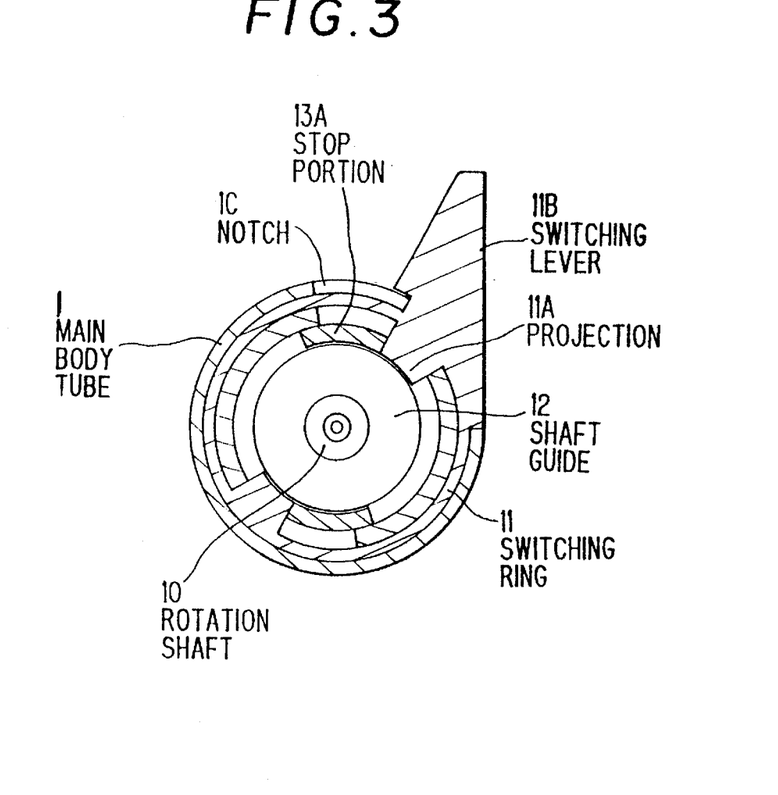
FIG. 3 is a cross-sectional view along the line A—A in FIG. 2.
Figure 4:
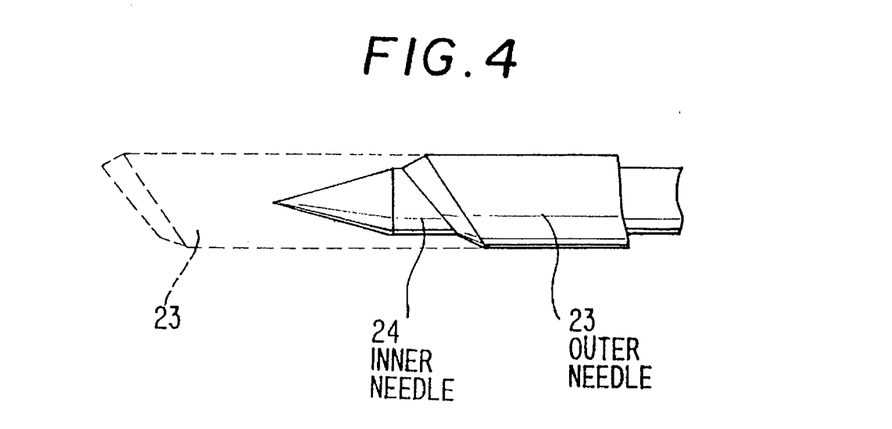
FIG. 4 is a explanatory view illustrating tips of inner and outer needles in a set of biopsy needles in the first embodiment according to the invention.

In FIGS. 1 to 3, there is shown a set of biopsy needles in the first embodiment according to the invention. The set of biopsy needles is composed of an inner needle holder 6 which has an inner needle base 22 at the front end to fix an inner needle 24, an outer needle holder 13 which is disposed outside the inner needle holder 6 and has an outer needle holder 21 at the front end to fix an outer needle 23, a main body tube 1 for gripping which is disposed outside the outer needle holder 13 to fix the inner needle holder 6 and to axially movably support the outer needle holder 13, a spring 9 which gives protrusion force to the outer needle holder 13 to protrude the outer needle 23 from the tip of the inner needle 24 as shown in FIG. 4, a magnet section 15 which holds the outer needle holder 13 at the position before protrusion against the protrusion force of the spring 9 and releases from holding by the rotation operation of a switching lever 11B, and a rotation shaft 10 which is fixed to the back end of the outer needle holder 13 with a screw 19 and gives rotation force to the outer needle holder 13 when the outer needle holder 13 moves axially.

The main body tube 1 is composed of a front tube section 1A which is provided with a slide stopper 2 and a back tube section 1B which is connected to back of the section 1A and, between these sections, there is provided a notch (an opening) 1C to control the range that the switching lever 11B can rotate. The front tube section 1A contains an adjusting ring 3 which is screwed at the tip thereof and can adjust the length of the protrusion of the outer needle 23, that is, the length of a clearance 3A according to the amount of screwing thereof, a cap 4 which is attached at the tip of the adjusting ring 3, and a scale 5 which is formed on the surface of the adjusting ring 3 and indicates the length of the protrusion of the outer needle 23. On the other hand, the back tube section 1B contains a back stopper 7 which is fixed by the screw 8 to the back end thereof, a metal fitting for fixing 20 which is connected inside the back stopper 7 and fixes the spring 9 and the rod of the inner needle holder 6 as described below, and a shaft guide 12 which is fixed inside the tip of the back tube section 1B, that is, inside the approximate center of the main body 1 by a screw 17 and has a pin 18 which protrudes to the center axis.

The inner needle holder 6 has a rod 6A which extends straightly to the back section of the main body tube 1 and is secured to the metal fitting for fixing 20 of the back stopper 7, whereby it is fixed to the main body tube 1.

The outer needle holder 13 has a stop section 13A in the form of a coaxial circular arc at the back end thereof which abuts on a projection 11A of a switching ring 11 as described below at the position before protrusion and is subjected to the rotation force of the switching ring 11 and abuts on the back end of the adjusting ring 3 when it protrudes according to the protrusion force of the spring 9, and it is provided with a rubber ring 16 as a bumper at a portion of the stop section 13A where abuts on the back end of the adjusting ring 3.

The switching lever 11B is shaped into one body with the switching ring 11 which is rotatably disposed inside the main body tube 1, and it is arranged so that it can rotate circumferentially.

The magnet section 15 is composed of a circular magnetic plate 15A which is fixed to the back end of the outer needle holder 13, that is, inside the stop section 13A via a yoke 14A and a circular magnetic plate 15B which is fixed to the shaft guide 12 via a yoke 14B. Each of the circular magnetic plates 15A and 15B is circumferentially provided with a plurality of N and S poles which are located alternately. The total number of the N and S poles is suitably six or eight. In accordance with the operation to rotate the switching ring 11, the outer needle holder 13 is rotated, that is, the circular magnetic plate 15A is rotated, whereby a relation of mutual pole provided with the two plates is varied to generate magnetic attractive or repulsive force between the two plates, so that the outer needle holder 13 is held at the position before protrusion or is released from holding. That is, opposing N pole to S pole causes the outer needle holder 13 to be held at the position before protrusion in accordance with the magnetic attractive force between the two plates, or opposing N pole to N pole or opposing S pole to S pole causes the outer needle holder 13 to be released from holding at the position before protrusion in accordance with the magnetic repulsive force between the two plates.

As the circular magnetic plates 15A and 15B, for example, a product which is manufactured by sintering a material having Nd(33%)-Fe(66%)-B(1%) composition and electroplating 15 micrometer in thickness of Ni film on the surface thereof, e.g., commercially available "NEO MAX40" manufactured by Sumitomo Tokushu Kinzoku K.K., is preferably employed. In such a magnet, magnetic properties of Br of 12.7 to 13.3 KG, bHc of 10.7 to 12.7 KOe, iHc>13.0 KOe and BHmax(maximum energy product) of 39.0 to 43.0 MGOe is obtained. Further, a Curie point of around 320 degree C. and use limit temperature of around 120 degree C. is obtained.

The rotation shaft 10 is provided with a groove 10A in spiral form on the outer surface into which the pin 19 of the shaft guide 12 as described above is engaged. That is, when it is protruded in accordance with the repulsive force of the spring 9, it is guided by the pin 18 so as to be rotated.

In operation, at first, the switching lever 11B is positioned at an initial position with the N and S poles provided with the circular magnetic plates 15A and 15B respectively opposed mutually, whereby the outer needle holder 13 is held at this position before protrusion against the repulsive force of the spring 9 and the tip of the inner needle 24 is projected from the outer needle 23 as shown by a full line in FIG. 4.

Next, a doctor punctures a predetermined part in a human body with the double needles while the tip of inner needle 24 is projected from the outer needle 23 while gripping the main body tube 1.

Thereafter, the switching ring 11 is rotated by operating the switching lever 11B to rotate the outer needle holder 13 via the stop portion 13A which abuts on the projection 11A in the switching ring 11, whereby the positions of the magnetic poles on the circular magnetic plate 15A which is fixed to the outer needle holder 13 are changed. That is, the same magnetic poles on the circular magnetic plates 15A and 15B are opposed to each other to generate repulsive force between the two plates. The holding of the outer needle holder 13 is released when the repulsive force is generated, whereby the outer needle holder 13 is pushed forward in accordance with the repulsive force of the spring 9. During that time, a rotation force is given to the outer needle holder 13 since the pin 18 is engaged in the spiral groove 10A provided with the rotation shaft 10. Accordingly, the outer needle 13 protrudes from the tip of the inner needle 14 as shown by the dotted line in FIG. 4 while being rotated.

When the outer needle 23 protrudes in this manner, the affected tissue in the human body is cut off by the outer needle and is collected inside the tip of the outer needle 23, then the double needles are pulled back from the human body to collect a piece of tissue. Since the outer needle 23 is protruded while being rotated when a piece of tissue is cut off by the outer needle 23, cutting off the affected tissue can be done easily and surely.

Figure 6:
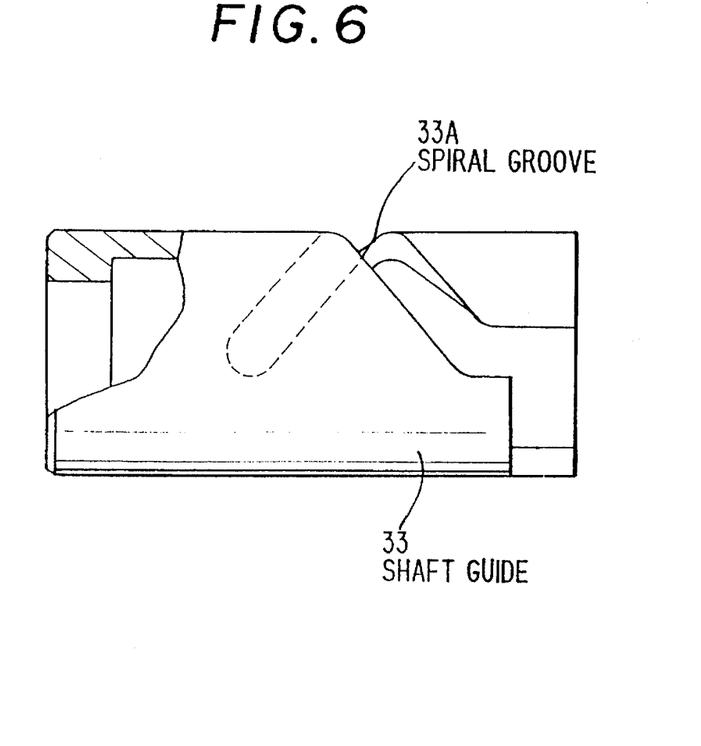
FIG. 6 is a partly cross-sectional view illustrating a shaft guide in a set of biopsy needles in the second embodiment according to the invention.
Figure 7:
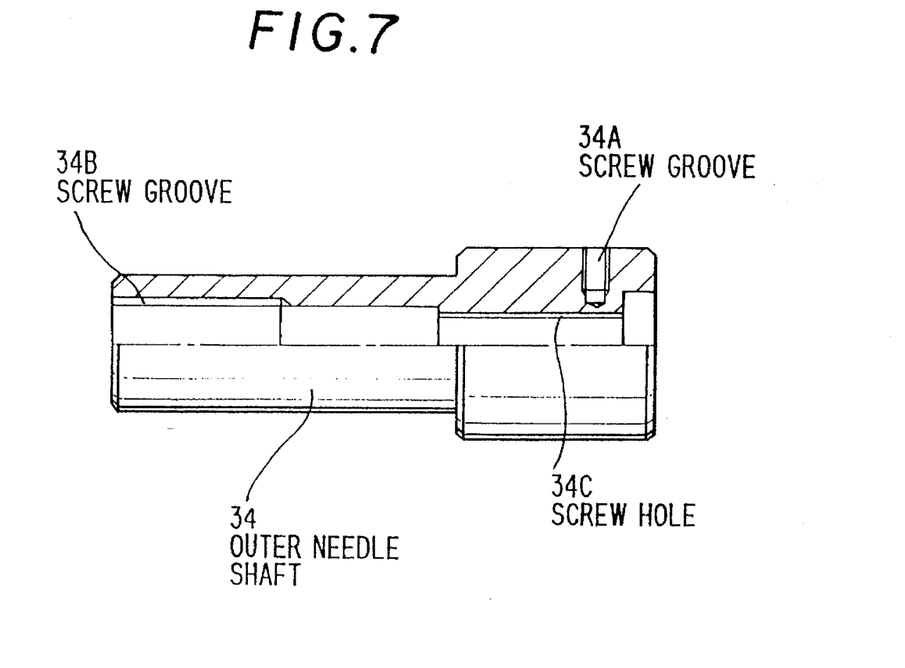
FIG. 7 is a partly cross-sectional view illustrating a outer needle shaft in a set of biopsy needles in the second embodiment according to the invention.
Figure 8:
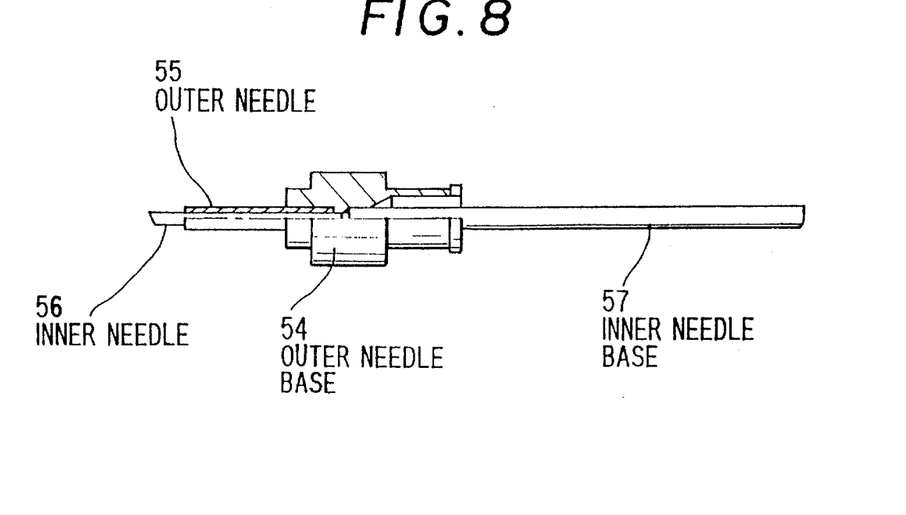
FIG. 8 is a partly cross-sectional view illustrating inner and outer needles in a set of biopsy needles in the second embodiment according to the invention.

In FIGS. 5 to 8, there is shown a set of biopsy needles in the second embodiment. The set of biopsy needles is composed of an outer needle shaft 34 which has a needle base fixing portion 31 at the front end for fixing an outer needle base 54 as shown in FIG. 8 and has a shaft 42 at the back end, a main body tube 32 for gripping which supports axially movably the outer needle shaft 34, a spring 44 and 45 which gives protrusion force to the outer needle shaft 34 to protrude an outer needle 55 from the tip of an inner needle 56, a magnet section 38 which holds the outer needle shaft 34 at the position before protrusion against the protrusion force of the spring 9 and releases from holding by the rotation operation of a switching lever 36, and a shaft guide 33 which is disposed on the circumference of the outer needle shaft 34 inside the main body tube 32 and gives rotation force to the outer needle shaft 34 when the outer needle shaft 34 protrudes.

Figure 5:
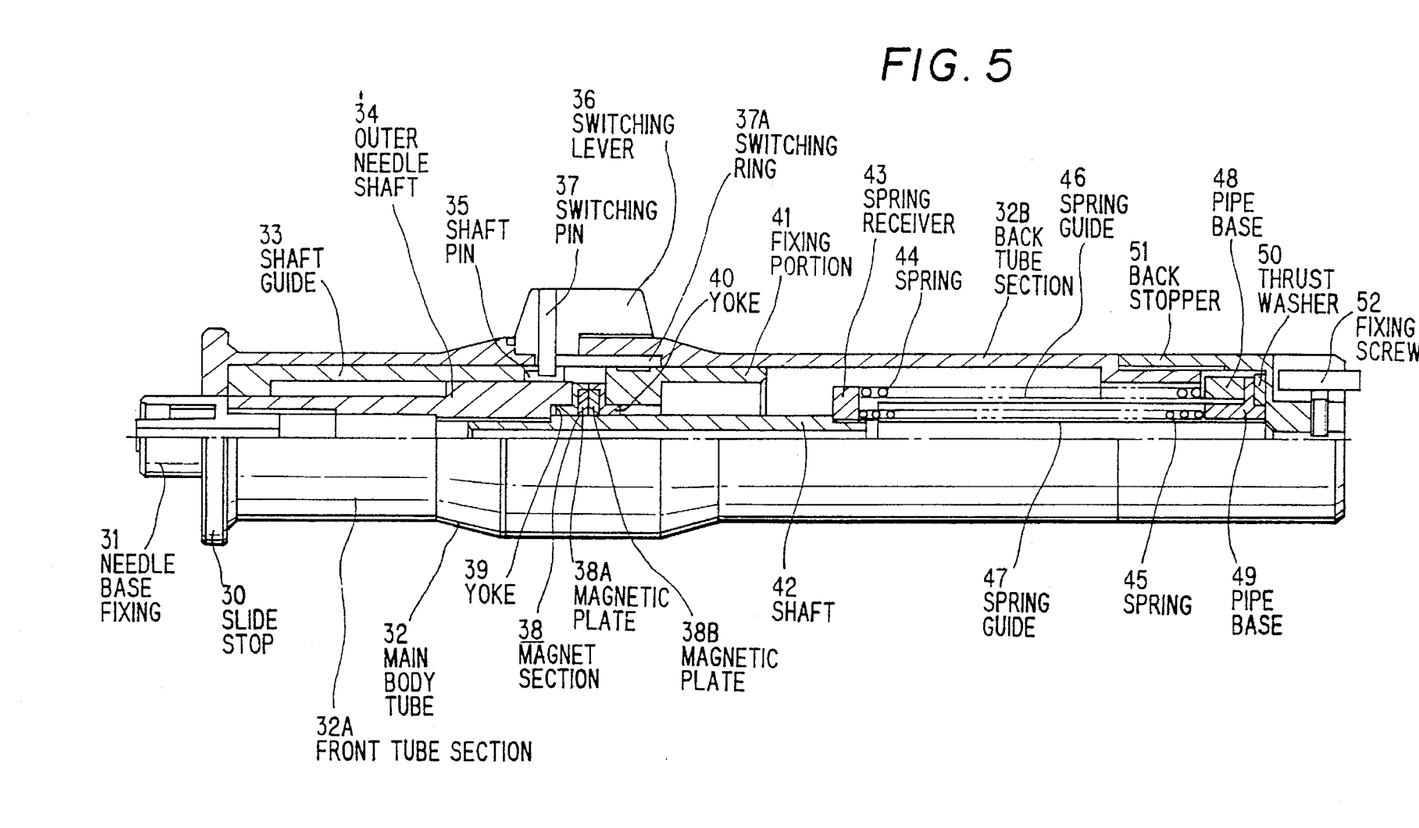
FIG. 5 is a partly cross-sectional view illustrating a set of biopsy needles in the second embodiment according to the invention.

The main body tube 32 is composed of a front tube section 32A which is provided with a slide stopper 30 and a back tube section 32B which is connected to back of the section 32A. A back stopper 51 has a fixing screw 52 which fixes an inner needle base 57 in the shape of a rod which extends through the outer needle base 54 and to the back end of the back tube section 32 B when the outer needle base 54 which has the outer needle 55 at the front end thereof as shown in FIG. 8 is fixed to the needle base fixing portion 31 which is located at the front end.

The shaft guide 33 is shaped into a hollow tube as shown in FIG. 6 and is provided with a spiral groove 33A which passes from inside through outside of the tube.

The outer needle shaft 34 is shaped into a tube which has a minor diameter portion and a major diameter portion as shown in FIG. 7 and is provided with a screw groove 34B inside the front section thereof into which the needle base fixing portion 31 is screwed and engaged and is provided with a screw groove 34C inside the back section thereof into which the shaft 42 is screwed and engaged and has a screw hole 34A into which the shaft pin 35 is fixed.

The switching lever 36 is connected to the switching ring 37A via a switching pin 37 which is rotatably disposed inside the main body tube 32 and is arranged so that it can rotate circumferentially. Further, the switching pin 37 abuts on the shaft pin 35, whereby the outer needle shaft 34 is rotated in accordance with the rotation of the switching lever 37.

The magnet section 38 is composed of a circular magnetic plate 38A which is fixed to the circumference of the shaft 42 via a yoke 39 and a circular magnetic plate 38B which is fixed via a yoke 40 to a fixing portion which is fixed to the inner surface of the back tube section 32B. As described in the first embodiment, each of the circular magnetic plates 38A and 38B is circumferentially provided with a plurality of N and S poles which are located alternately. The total number of the N and S poles is suitably six or eight. In accordance with the operation of rotating the switching lever 36, the shaft 42 is rotated, that is, the circular magnetic plate 38A is rotated, whereby a relation of mutual pole on the two plates is varied to generate magnetic attractive or repulsive force between the two plates, so that the outer needle shaft 34 is held at the position before protrusion or is released from holding.

The spring 44 and 45 is inserted between a spring receiver 43 which is screwed and engaged into the back end of the shaft 42 and a pipe base 48 and 49 which is shaped into one body with a spring guide 46 and 47, whereby it is arranged so that the outer needle shaft 34 can be protruded when the repulsive force is generated at the magnet section 38 as described above. 50 is a thrust washer which is disposed between the pipe base 49 and the back stopper 51.

In the operation of the second embodiment, at first, the N and S poles provided with the circular magnetic plates 15A and 15B respectively are opposed mutually, whereby the outer needle shaft 34 is held at the position before protrusion against the protrusion force of the spring 9 and the tip of the inner needle 56 is projected from the outer needle 55.

Next, a doctor punctures a predetermined part in a human body by the double needles which the tip of inner needle 56 is projected from the outer needle 55 while gripping the main body tube 32.

Thereafter, the switching lever 36 is rotated circumferentially to rotate the outer needle shaft 34 via the shaft pin 35 which abuts on the switching pin 37, whereby the positions of the magnetic poles on the circular magnetic plate 38A which is fixed on the circumference of the shaft 42 are changed. That is, the same magnetic poles on each of the circular magnetic plate 15A and 15B are opposed to generate repulsive force between the two plates. The holding of the outer needle shaft 34 is released when the repulsive force is generated, whereby the shaft pin 35 on the outer needle shaft 34 is pushed forward in accordance with the repulsive force of the spring 44 and 45. On that time, rotation force is given to the outer needle shaft 34 since the shaft pin 35 on the shaft 34 moves along the spiral groove 33A. Accordingly, the outer needle 55 is protruded from the tip of the inner needle 56 while being rotated.

Also in this embodiment, the outer needle 55 is protruded while being rotated, so that cutting off the affected tissue can be done easily and surely to provide with enhanced reliability.

Figure 9:
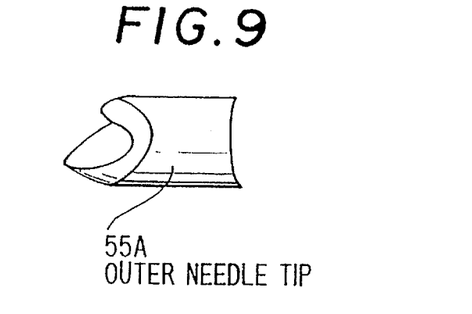
FIG. 9 is a explanatory view illustrating a set of biopsy needles in the third embodiment according to the invention.
Figure 10:
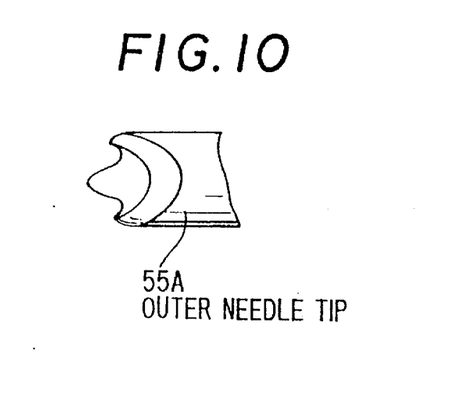
FIG. 10 is a explanatory view illustrating a set of biopsy needles in the forth embodiment according to the invention.

Furthermore, the shape of the tip 55 A of the outer needle 55 as shown FIGS. 9 and 10 can be suitably employed to enhance the performance to cut off tissue.

Although the invention has been described with respect to specific embodiment for complete and clear disclosure, the appended claims are not to be thus limited but are to be construed as embodying all modification and alternative constructions that may occur to one skilled in the art which fairly fall within the basic teaching herein set forth.

What is claimed is:

1. A set of biopsy needles having double biopsy needles including an outer needle in the form of a hollow tube and an inner needle inserted into said outer needle, which set is punctured into a predetermined part in a human body and thereafter said outer needle is pushed forward to protrude beyond a tip of said inner needle, whereby a piece of tissue in said predetermined part in a human body can be collected inside a tip of said outer needle, the set of biopsy needles comprising:

a first shaft member, for said inner needle, having a needle base for fixing said first shaft member of said inner needle in said set of biopsy needles;

a second shaft member, for said outer needle, coaxially encircling said first shaft member for the inner needle, said second shaft member having a needle base fixed to said second shaft member of said outer needle;

a gripping member, located outside a circumference of said second shaft member for the outer needle, said first shaft member for the inner needle being fixed to said gripping member and said second shaft member for the outer needle being axially moveably supported within said gripping member;

an actuating member within said gripping member which gives protrusion force to said second shaft member for the outer member so that said outer needle can be made to protrude beyond the tip of said inner needle;

holding means for holding said second shaft member for the outer needle at a fixed position before protrusion against said protrusion force of said actuating member, said holding means releasing said second shaft member for the outer needle from the fixed position before protrusion upon exertion of an outside force upon the holding means; and a rotation generating means for giving a rotation force to said second shaft member for the outer needle, said outer needle protruding beyond the tip of said inner needle while being rotated when said shaft member for the outer needle is moved axially by said protrusion force of said actuating member.

2. The set of biopsy needles according to claim 1, wherein said holding means comprises:

a first circular magnetic plate which is fixed to said second shaft member for the outer needle and can be rotated by said exertion of said outside force;

a second circular magnetic plate which is fixed at a predetermined position relative to said gripping member and said first shaft member; and wherein each of said first and second circular magnetic plates is provided with a plurality of N and S magnetic poles which are located alternately about a circumference thereof, said first and second magnetic plates being opposed to each other with said magnetic poles interacting magnetically.

3. The set of biopsy needles according to claim 1, wherein said rotation generating means comprises:

a guide pin which is attached inside said gripping member for operation; and a spiral groove which is formed on the circumference of said second shaft member for the outer needle and is engaged with said guide pin.

* * * * *